(12) United States Patent
Lee

(10) Patent No.: US 12,308,137 B1
(45) Date of Patent: May 20, 2025

(54) SYSTEM AND METHOD FOR A TEMPORARY BIOLOGICAL CIRCUIT

(71) Applicant: Fully Loaded Electronics, LLC, Everett, WA (US)

(72) Inventor: Robin Lee, Mill Creek, WA (US)

(73) Assignee: Fully Loaded Electronics, LLC, Everett, WA (US)

( * ) Notice: Subject to any disclaimer, the term of this patent is extended or adjusted under 35 U.S.C. 154(b) by 0 days.

(21) Appl. No.: 18/660,049

(22) Filed: May 9, 2024

(51) Int. Cl.
*H01B 1/20* (2006.01)
*B05D 3/10* (2006.01)
*C12N 1/20* (2006.01)
*H01B 1/12* (2006.01)
*H01B 13/00* (2006.01)

(52) U.S. Cl.
CPC ............. *H01B 1/12* (2013.01); *B05D 3/107* (2013.01); *C12N 1/205* (2021.05); *H01B 13/0036* (2013.01)

(58) Field of Classification Search
CPC ... H01B 1/20; H01B 1/22; H01B 1/24; H01B 13/0036; C12N 1/20; C12N 1/205; C09D 5/008; C09D 103/02–20; B05D 3/107
See application file for complete search history.

(56) References Cited

U.S. PATENT DOCUMENTS 9,175,179 B2 * 11/2015 Troutman ............... C08B 31/04

FOREIGN PATENT DOCUMENTS

| CN | 117672596 A | * | 3/2024 | |
| KR | 20230134042 | * | 9/2023 | |
| WO | WO-0206507 A1 | * | 1/2002 | ........... A61K 9/4816 |

OTHER PUBLICATIONS

Tan et al "Biodegradable electronics: cornerstone for sustainable electronics and transient applications", Cite this: J. Mater. Chem. C, 2016,4, 5531.*
Bonne et al "Biomaterials and Electroactive Bacteria for Biodegradable Electronics", (2022) Biomaterials and Electroactive Bacteria for Biodegradable Electronics. Front. Microbiol. 13:906363.*
Xiang et al "Green flexible electronics based on starch", npj Flexible Electronics (2022) 6:15 ; https://doi.org/10.1038/s41528-022-00147-x.*
Jaiswal et al "Biodegradable Cellulose Nanocomposite Substrate for Recyclable Flexible Printed Electronics", Adv. Electron. Mater. 2023, 9, 2201094 (12 pages).*

* cited by examiner

Primary Examiner — Mark Kopec
(74) Attorney, Agent, or Firm — Seed IP Law Group LLP

(57) ABSTRACT

A system and method for a temporary circuit that is created implanting a biodegradable paste at one or more connection points of a circuit wherein the connection points complete the circuit and make the connection work, wherein the biodegradable paste is dissolved by applying a bacteria to remove the biodegradable paste.

20 Claims, 2 Drawing Sheets

Create Gaps in the Circuit 201 → Position Biodegradable Paste into the gaps 202 → Spray Bacteria on Biodegradable Paste 203

FIG. 2

SYSTEM AND METHOD FOR A TEMPORARY BIOLOGICAL CIRCUIT

FIELD OF THE DISCLOSURE

This relates generally to temporary circuitry and more particularly the use of biodegradable paste for temporary circuitry connections.

BACKGROUND

Temporary circuitry may provide a high level of security for sensitive information. In military or intelligence applications, these circuits can be programmed to destroy themselves, ensuring that sensitive data does not fall into the wrong hands. This is particularly useful in scenarios where recovery of the device by unauthorized personnel is a risk. There have been previous attempts at temporary circuits but they are complex or contribute to electronic waste. These devices can take hundreds of years to decompose in landfills, and often contain hazardous materials. Thus exists the need for a temporary circuit that is designed to decompose or dissolve after a predetermined period, significantly reducing the environmental impact while proving advantageous in the field of security.

SUMMARY

The present invention is directed to a system and method that begins by microscopically breaking a circuit at one or more points. This may be done with a robotic arm that is designed to make minute cuts or melt a circuit line or any other method known by those of ordinary skill in the art. When it is desired to temporarily patch the circuit line, the biopaste is used to fill the gap in the circuit line. After the circuit line has served its purpose of transporting power or data, the user may then turn off the device, then spray a biopaste-eating bacterial aerosol into the electronic device whereby after a predesignated amount of time the circuit line is now back to being severed with the biopaste being eaten by bacteria.

DESCRIPTION OF THE DRAWINGS

Embodiments of the present disclosure are described in detail below with reference to the following drawings. These and other features, aspects, and advantages of the present disclosure will become better understood with regard to the following description, appended claims, and accompanying drawings. The drawings described herein are for illustrative purposes only of selected embodiments and not all possible implementations and are not intended to limit the scope of the present disclosure.

FIG. 2 is a flow chart for the temporary circuit.

DETAILED DESCRIPTION

Figure 1:
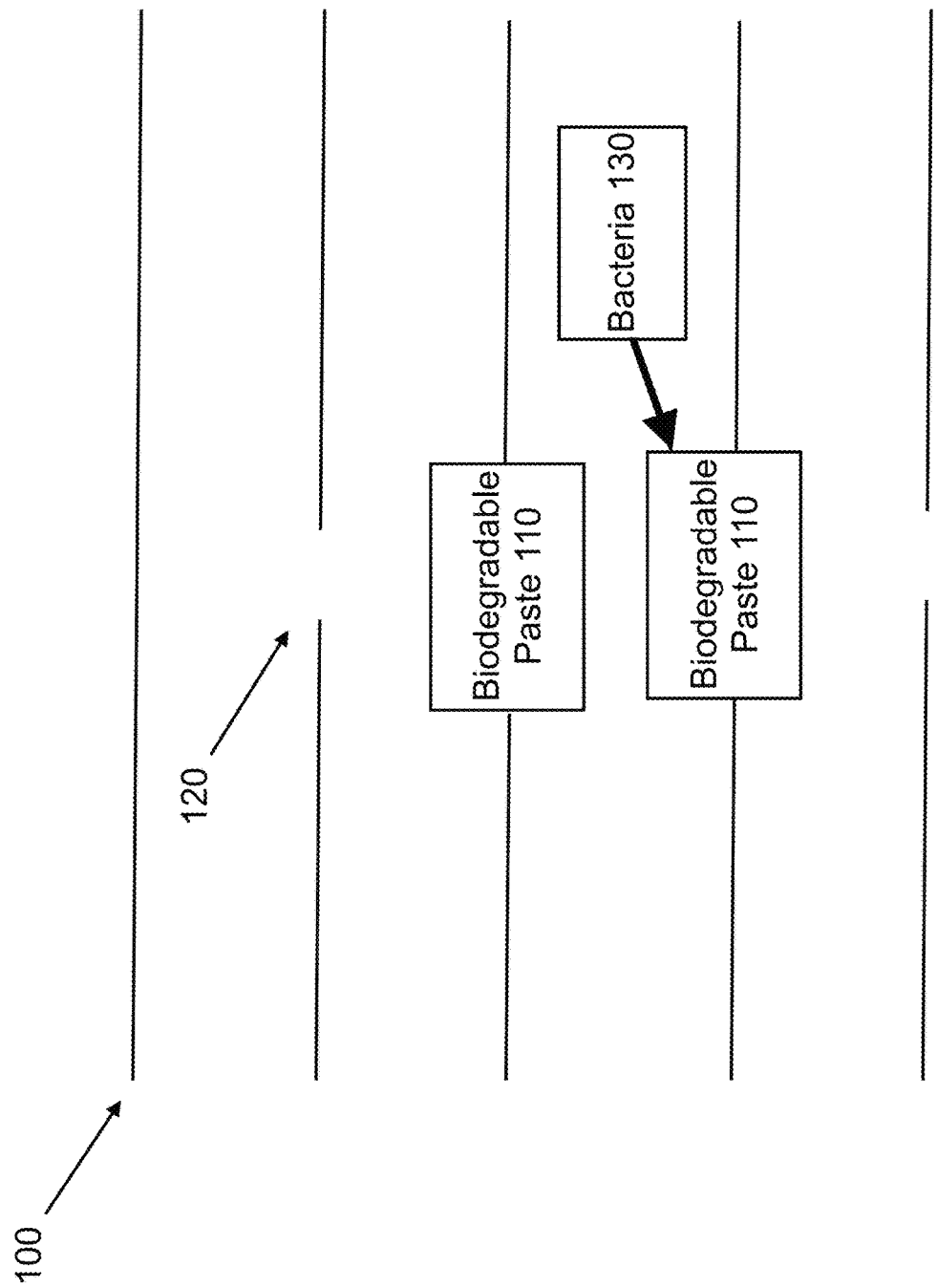
FIG. 1 is a front view of an exemplary block diagram of the temporary circuit in accordance with an illustrative embodiment.

The following description and drawings are illustrative and are not to be construed as limiting. Numerous specific details are described to provide a thorough understanding of the disclosure. However, in certain instances, well-known or conventional details are not described in order to avoid obscuring the description. References to one or another embodiment in the present disclosure can be, but not necessarily are, references to the same embodiment; and, such references mean at least one of the embodiments.

Reference in this specification to "one embodiment" or "an embodiment" means that a particular feature, structure, or characteristic described in connection with the embodiment is included in at least one embodiment of the disclosure. Appearances of the phrase "in one embodiment" in various places in the specification do not necessarily refer to the same embodiment, nor are separate or alternative embodiments mutually exclusive of other embodiments. Moreover, various features are described which may be exhibited by some embodiments and not by others.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks: The use of highlighting has no influence on the scope and meaning of a term; the scope and meaning of a term is the same, in the same context, whether or not it is highlighted. It will be appreciated that the same thing can be said in more than one way.

The present description includes one or more embodiments for a system and method for creating temporary circuit by microscopically breaking down one or more points on a circuit using a robotic arm or other apparatus creating gaps. On embodiment of the temporary circuit is illustrated in FIG. 1 as temporary circuit 100. A biodegradable paste 110 such as but not limited to a biodegradable potato paste may then be inserted at one or more removed points 120 or the gaps of the circuit by adhesive or welding or other types of fasteners wherein the connection points complete the circuit and make the connection work. The biodegradable paste 110 is then dissolved by spraying or applying a bacteria 130 to remove the biodegradable paste 110.

The biodegradable potato paste 110 may be an eco-friendly material primarily derived from potatoes. In one non-limiting embodiment, the biodegradable potato paste 110 may include potato starch which is a biopolymer that forms the base of the paste 110 having high amylose and amylopectin content that provides strength and flexibility to the connection point. The biodegradable potato paste 110 may include water used as a solvent to help form the paste 110 and glycerol or other plasticizers which are used to improve the flexibility and prevent the connection points 120 from becoming too brittle.

The biodegradable paste 110 (currently made of potatoes, but can be made of any matter that can be decomposed by bacteria 130) may also include natural fibers such as cellulose, hemp, or flax to enhance the mechanical properties of the material, such as tensile strength and durability. The biodegradable potato paste 110 may also include natural additives such antimicrobial agents or natural dyes can be included to provide additional functionalities or aesthetics. This material of the potato paste 110, due to its biodegradable nature, decomposes much faster than traditional plastics or metals when exposed to natural environmental conditions. The biodegradable potato paste 110 may be mixed in with any number of conductive materials such as carbon particles, graphene, or metallic fibers to impart electrical conductivity. The biodegradable potato paste 110 may then be used to create pathways on a substrate by a stencil or printing technique to apply the paste 110 in the desired pattern at different connection points 120.

The decomposition of biodegradable paste 110 may include a plurality of different types of bacteria 130, each playing specific roles in the breakdown process. The types of bacteria 130 involved may vary based on environmental conditions such as temperature, pH, and moisture levels. Some groups of bacteria 130 involved in this process may include: amylolytic bacteria which specialize in breaking down starch into simpler sugars. They produce amylase, an enzyme that catalyzes the hydrolysis of starch. Examples may include members of the genera *Bacillus, Streptomyces,* and *Clostridium*. Another group may be cellulolytic bacteria whereby when the biodegradable paste 110 contains cellulose fibers (as fillers or reinforcements), these bacteria break down cellulose into glucose units. Examples may include *Cellulomonas* and *Clostridium.*

Another group may be lactic acid bacteria which can ferment simple sugars into lactic acid. Examples may include *Lactobacillus*. Another group may be acetogenic bacteria that convert organic acids and alcohols produced during earlier decomposition stages into acetic acid. Examples may include *Acetobacter*. Another group may be methanogenic bacteria that can convert acetic acid into methane. Examples include *Methanobacterium* and *Methanosarcina*. Another group may be *Pseudomonas* which can degrade a wide range of organic compounds, contributing significantly to the biodegradation process. Another group may be Enterobacteriaceae. Examples may include *Escherichia coli*. The specific composition and activity of these microbial communities may vary greatly depending on the specific formulation of the biodegradable paste 110 and environmental conditions. Overall, these bacteria work synergistically to break down complex organic compounds into simpler, environmentally benign substances, completing the natural cycle of organic matter decomposition and disabling the circuit by dissolving the connection point.

During operation, the moisture in the environment aids bacteria in breaking down the potato starch present in the biodegradable paste 110, such as enzymes secreted by bacteria start the hydrolysis process, breaking down long polymer chains into simpler, smaller molecules like monosaccharides.

The simpler molecules produced during hydrolysis are further broken down by other bacteria. These bacteria convert these molecules into organic acids, alcohols, hydrogen, and carbon dioxide. This step is often characterized by a decrease in pH due to the production of acidic compounds.

The organic acids and alcohols generated in the acidogenesis phase are then converted into acetic acid, hydrogen, and carbon dioxide by acetogenic bacteria. This step is crucial for preparing the substrates for the final phase of decomposition.

In the final step, methanogenic bacteria convert the products from acetogenesis (mainly acetic acid) into methane and carbon dioxide. This phase is essential in anaerobic decomposition (decomposition in the absence of oxygen). The entire process is facilitated by microbial activity and is influenced by environmental factors such as temperature, oxygen availability, moisture, and pH levels.

In the case of biodegradable potato paste 110, its organic components (starch and other biodegradable additives) are readily metabolizable by microbes, making it an efficient substrate for decomposition. The end products of this decomposition process are biomass, water, carbon dioxide (or methane in anaerobic conditions), and other minor compounds, all of which are environmentally friendly and contribute to the nutrient cycle. This contrasts sharply with the decomposition of traditional plastics, which can take hundreds of years and often leave behind harmful residues.

During operation, as illustrated in FIG. 2, one or more gaps 120 may be created in circuit 100 at step 201. The circuit 100 may then be completed with a biodegradable paste 110 at connect points in the one or more gaps to complete the circuit at step 202. Once the circuit 100 is desired to be dissolved, the user may remove biodegradable paste 110 with a bacteria 130 at step 203.

Biodegradable paste 110 110 may be inserted into any type of circuit. The circuit may have a power source that provides the energy for the circuit such as batteries and power supplies. The circuit may have conductors usually made wires made of copper or aluminum, whereby the conductors connect the components of the circuit and allow electric current to flow through them. The circuit may have resistors that are components that restrict the flow of electric current, thereby controlling the voltage and current in the circuit.

The circuit may have capacitors which are components that store and release electrical energy. They are used to smooth out electrical signals or store energy temporarily. The circuit may have a may have inductors which are coils of wire that generate a magnetic field when electric current flows through them. Inductors are used to filter signals and store energy in magnetic fields. The circuit may have a diodes which are components that allow current to flow in only one direction, functioning somewhat like a one-way valve for electricity.

The circuit may have transistors that are semiconductor devices that can act as switches or amplifiers in circuits. They are fundamental in controlling the flow of electrical current. Switches: Devices that can open or close the circuit, allowing or stopping the flow of current. The circuit may have relays which are electrically operated switches that use an electromagnet to mechanically operate a switch for controlling a larger current with a smaller one.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the invention for various embodiments with various modifications as are suited to the particular use contemplated. The present invention according to one or more embodiments described in the present description may be practiced with modification and alteration within the spirit and scope of the appended claims. Thus, the description is to be regarded as illustrative instead of restrictive of the present invention.

What is claimed is:

1. A method for creating a temporary circuit, the method comprising:

opening a circuit by creating one or more gaps in the circuit;

completing the circuit with a biodegradable paste at connect points in the one or more gaps; and applying, to the biodegradable paste, a combination of one or more bacteria configured to decompose the biodegradable paste, wherein applying the combination of one or more bacteria to the biodegradable paste causes the circuit to open.

2. The method of claim 1, wherein the biodegradable paste includes a potato paste.

3. The method of claim 2, wherein the potato paste includes starch, water, and natural fibers.

4. The method of claim 3, further comprising: mixing the potato paste with a conductive material.

5. The method of claim 1, wherein the biodegradable paste includes starch, the combination of one or more bacteria includes amylolytic bacteria, and wherein removing the biodegradable paste includes:
converting, using the amylolytic bacteria, the starch into simple sugars.

6. The method of claim 5, wherein the combination of one or more bacteria includes lactic acid bacteria, and wherein removing the biodegradable paste includes:
converting, using the lactic acid bacteria, the simple sugars into lactic acid.

7. The method of claim 6, wherein the combination of one or more bacteria includes acetogenic bacteria, and wherein removing the biodegradable paste includes:
converting, using the acetogenic bacteria, the lactic acid into acetic acid.

8. The method of claim 7, wherein the combination of one or more bacteria includes methanogenic bacteria, and wherein removing the biodegradable paste includes:
converting, using the methanogenic bacteria, the acetic acid into methane.

9. The method of claim 1, wherein the biodegradable paste includes cellulose, the combination of one or more bacteria includes cellulolytic bacteria, and wherein removing the biodegradable paste includes:
converting, using the cellulolytic bacteria, the cellulose into glucose.

10. The method of claim 1, wherein the combination of one or more bacteria includes Enterobacteriaceae.

11. A system for a temporary circuit, the system comprising:
a biodegradable paste at connect points to complete a circuit, wherein the biodegradable paste includes starch; and
a combination of one or more bacteria configured to be applied to the biodegradable paste to decompose the biodegradable paste, wherein application of the combination of one or more bacteria to the biodegradable paste causes the circuit to open and wherein the combination of one or more bacteria includes at least one of:
a first bacteria to convert the starch of the biodegradable paste into simple sugars;
a second bacteria to convert the simple sugars into lactic acid;
a third bacteria to convert the lactic acid into acetic acid; or
a fourth bacteria to convert the acetic acid into methane.

12. The system of claim 11, wherein the biodegradable paste includes a potato paste.

13. The system of claim 12, wherein the potato paste includes starch, water, and natural fibers.

14. The system of claim 11, wherein the biodegradable paste includes a conductive material.

15. The system of claim 11, wherein the first bacteria includes amylolytic bacteria.

16. The system of claim 11, wherein the biodegradable paste includes cellulose, and the combination of one or more bacteria includes cellulolytic bacteria.

17. The system of claim 11, wherein the second bacteria includes lactic acid bacteria.

18. The system of claim 11, wherein the third bacteria includes acetogenic bacteria.

19. The system of claim 11, wherein the fourth bacteria includes methanogenic bacteria.

20. The system of claim 11, wherein the combination of one or more bacteria includes Enterobacteriaceae.

* * * * *